United States Patent [19]
Garcea et al.

[11] Patent Number: 6,165,471
[45] Date of Patent: *Dec. 26, 2000

[54] HOMOGENEOUS HUMAN PAPILLOMAVIRUS CAPSOMERE CONTAINING COMPOSITIONS, METHODS FOR MANUFACTURE, AND USE THEREOF AS DIAGNOSTIC, PROPHYLACTIC OR THERAPEUTIC AGENTS

[75] Inventors: Robert L. Garcea, Boulder, Colo.; JoAnn A. Suzich, Washington Grove; Michael P. McCarthy, Poolesville, both of Md.; Robert C. Rose, Dansville, N.Y.

[73] Assignees: University of Colorado, University Technology Corporation, Boulder, Colo.; MedImmune, Inc., Gaithersburg, Md.; University of Rochester, Office of Research and Project Administration and Institute of Higher Education, Rochester, N.Y.

[ * ] Notice: This patent is subject to a terminal disclaimer.

[21] Appl. No.: 09/109,036

[22] Filed: Jul. 2, 1998

Related U.S. Application Data

[60] Provisional application No. 60/051,678, Jul. 3, 1997.
[51] Int. Cl.[7] ................................................ A61K 39/12
[52] U.S. Cl. ................................... 424/186.1; 424/192.1; 424/204; 424/1; 424/199.1; 435/235.1; 435/69.1; 435/69.3; 435/320.1; 536/23.72; 536/23.4
[58] Field of Search .......................... 424/186.1, 192.1, 424/204.1, 199.1; 435/235.1, 69.1, 69.3, 320.1, 348; 536/23.72, 23.4

[56] References Cited

FOREIGN PATENT DOCUMENTS

WO94/05792  3/1994  WIPO .

OTHER PUBLICATIONS

LI et al. J. of Virology, Apr. 1997, vol. 71, No. 4, pp. 2988–2995.

Painstil et al. Virology, 1996, vol. 223, pp. 238–244, Jan. 1996.

*Primary Examiner*—Ali Salimi
*Attorney, Agent, or Firm*—Burns, Doane, Swecker & Mathis, L.L.P.

[57] ABSTRACT

The present invention relates to stable HPV capsomeres which express at least one virus-neutralizing conformational epitope of a native HPV L1 protein which are substantially incapable of assembly into virus-like particles. These capsomeres, because of their smaller size, and immunogenic properties are well suited for use in HPV vaccines and as diagnostic agents. Moreover, because of their smaller size (relative to VLPs), these stable capsomeres may be easily purified and should result in HPV vaccines of enhanced homogeneity.

35 Claims, 7 Drawing Sheets

HOMOGENEOUS HUMAN PAPILLOMAVIRUS CAPSOMERE CONTAINING COMPOSITIONS, METHODS FOR MANUFACTURE, AND USE THEREOF AS DIAGNOSTIC, PROPHYLACTIC OR THERAPEUTIC AGENTS

This application claims priority under 35 U.S.C. §§119 and/or 365 to Ser. No. 60/051,678 filed in the United States on Jul. 3, 1997; the entire content of which is herby incorporated by reference.

FIELD OF THE INVENTION

The present invention relates to stable human papillomavirus (HPV) capsomeres and compositions containing produced by enzymatic, chemical and/or recombinant methods. Such HPV capsomeres and compositions containing are useful, e.g., as vaccines for conferring protection against human papillomavirus infection and as diagnostic agents for detection of antibodies specific to HPV L1 proteins. The present invention further relates to modified HPV L1 nucleic acid sequences which have been modified by site specific mutagenesis and/or deletion in order to favor the formation of stable capsomeres which are substantially incapable of assembly into virus-like particles.

BACKGROUND OF THE INVENTION

Papillomaviruses infect a wide variety of different species of animals including humans. Infection is typically characterized by the induction of benign epithelial and fibroepithelial tumors, or warts at the site of infection. Each species of vertebrate is infected by a distinct group of papillomavirus, each papillomavirus group comprising several different papillomavirus types. For example, more than sixty different human papillomavirus (HPV) genotypes have been isolated. Papillomaviruses are highly species-specific infective agents. For example, canine and rabbit papillomaviruses cannot induce papillomas in heterologous species such as humans. Neutralizing immunity to infection against one papillomavirus type generally does not confer immunity against another type, even when the types infect a homologous species.

In humans, papillomaviruses cause genital warts, a prevalent sexually transmitted disease. HPV types 6 and 11 are most commonly associated with benign genital warts condyloma acuminata. Genital warts are very common and sub-clinical or inapparent HPV infection is even more common than clinical infection. While most HPV induced lesions are benign, lesions arising from certain papillomavirus types, e.g., HPV-16 and HPV-18, can undergo malignant progression. Moreover, infection by one of the malignancy associated papillomavirus types is considered to be a significant risk factor in the development of cervical cancer, the second most common cancer in women worldwide. Of the HPV genotypes involved in cervical cancer, HPV-16 is the most common, being found in about 50% of cervical cancers.

In view of the significant health risks posed by papillomavirus infection generally, and human papillomavirus infection in particular, various groups have reported the development of recombinant papillomavirus antigens and their use as diagnostic agents and as prophylactic vaccines. In general, such research has been focused toward producing prophylactic vaccines containing the major capsid protein (L1) alone or in combination with the minor capsid protein (L2). For example, Ghim et al, *Virology*, 190:548–552 (1992) reported the expression of HPV-1 L1 protein using a vaccinia expression in Cos cells which displayed conformational epitopes and the use thereof as a vaccine or for serological typing or detection. This work is also the basis of a patent application, U.S. Ser. No. 07/903,109, filed Jun. 25, 1992 (abandoned in favor of U.S. Serial No. 08/216,506, filed on March 22, 1994), which has been licensed by the assignee of this application. Also, Suzich et al, *Proc. Natl. Acad. Sci., U.S.A.*, 92:11553–11557 (1995) report that the immunization of canines with a recombinant COPV expressed in a baculovirus/insect cell system completely prevented the development of viral mucosal papillomas. These results are important given the significant similarities between many HPVs and COPV. For example, COPV, similar to HPVs associated with anogenital and genital papillomas cancer, infects and induces lesions at a mucosal site. Also, the L1 sequences of COPV shares structural similarities to HPV L1 sequences both at the level of DNA and protein. Given these similarities, the COPV/beagle model is useful for investigation of L1 protein containing vaccines, e.g., investigation of the protective immune response, protection from natural infection and optimization of vaccination protocols. (Id.)

Also, a research group from the University of Rochester reported the production of human papillomavirus major capsid protein (L1) and virus-like particles using a baculovirus/insect cell expression system. (Rose et al, University of Rochester, WO 94/20137, published on Sep. 15, 1994). In particular, they reported the expression of the L1 major capsid protein of HPV-6 and HPV-11 and the production of HPV-6, HPV-11, HPV-16 and HPV-18 virus-like particles.

Further, a University of Queensland research group also purportedly disclosed the recombinant manufacture of papillomavirus L1 and/or L2 proteins and virus-like particles as well as their potential use as vaccines. (Frazer et al, WO 93/02189, published on Feb. 4, 1993).

Still further, a United States government research group reported recombinant papillomavirus capsid proteins purportedly capable of self-assembly into capsomere structures and viral capsids that comprise conformational antigenic epitopes. (U.S. Pat. No. 5,437,951, Lowy et al, issued on Aug. 1, 1995.) The claims of this patent are directed to a specific HPV-16 DNA sequence which encodes an L1 protein capable of self-assembly and use thereof to express recombinant HPV-16 capsids containing said HPV-16 L1 protein.

With respect to HPV capsid protein containing vaccines, it is widely accepted by those skilled in the art that a necessary prerequisite of an efficacious HPV L1 major capsid protein-based vaccine is that the L1 protein present conformational epitopes expressed by native human papillomavirus major capsid proteins (See, e.g., Hines et al, *Gynecologic Oncology*, 53:13–20 (1994); Suzich et al, *Proc. Natl. Acad. Sci., U.S.A.*, 92:11553–11557 (1995)).

Both non-particle and particle recombinant HPV L1 proteins that present native conformational HPV L1 epitopes have been reported in the literature. It is known that L1 is stable in several oligomeric configurations, e.g., (i) capsomeres which comprise pentamers of the L1 protein and (ii) capsids which are constituted of seventy-two capsomeres in a T=7 icosahedron structure. Also, it is known that the L1 protein, when expressed in eukaryotic cells by itself, or in combination with L2, is capable of efficient self-assembly into capsid-like structures generally referred to as virus-like particles (VLPs).

VLPs have been reported to be morphologically and antigenically equivalent to authentic virions. Moreover, immunization with VLPs has been reported to elicit the production of virus-neutralizing antibodies. More specifically, results with a variety of animal papillomaviruses (canine oral papillomavirus and bovine papillomavirus-4) have suggested that immunization with VLPs results in protection against subsequent papillomavirus infection. Consequently, VLPs composed of HPV L1 proteins have been proposed as vaccines for preventing diseases associated with human papillomavirus infections.

Additional studies have examined the effects of L1 deletions on capsid assembly. For example, Paintsil et al recently reported that certain carboxy-terminal residues of the BPV-1 L1 protein are not required for capsid formation. (Paintsil et al, *Virol.*, 223:238–244 (1996)). Moreover, at page 239, a schematic summary of the results obtained upon expression of various BPV L1 deletions generated by PCR mutagenesis is provided. In particular, this summary indicates whether such fragments result in proper (icosahedon) capsids, aberrant capsids, unstructured L1 aggregates or capsomeres. (Id.) Also, Paintsil et al teach a specific carboxy-deletion wherein residues 451–495 ($\Delta$C1) of the BPV-1 L1 protein were deleted. However, there is no indication that the resultant capsomeres present conformational epitopes of native BPV-1 or whether they elicited neutralizing antisera. Also, Paintsil et al (Id.), further notes at page 21, that "these truncation results suggested that deletion of a more conserved region upstream of [amino acid] 471 (FIG. 4) completely perturbs the proper folding of the L1 protein". Therefore, these results would teach against making modifications involving significant carboxy-terminal deletions. Also, their experiments are limited to BPV-1 L1 deletions and mutations.

Therefore, notwithstanding what has been previously reported, there still exists a need in the art for novel HPV major capsid protein containing compositions that present conformational epitopes associated with native (wild-type) HPVs, and methods for their manufacture.

OBJECTS OF THE INVENTION

It is an object of the invention to provide stable HPV capsomeres which present conformational epitopes expressed by authentic (wild-type, infectious) HPV virions.

It is a more specific object of the invention to provide stable HPV capsomeres which present at least one virus-neutralizing conformational epitope(s) expressed by authentic HPV virions by enzymatic (trypsin) digestion of purified HPV capsomere and/or virus-like particles.

It is another more specific object of the invention to produce stable HPV capsomeres by chemical methods, i.e., by "capping-off" one or more cysteine residues, e.g., by reacting reduced cysteine residues with compounds that prevent oxidation of sulfhydryls, e.g., alkylating agents, thereby preventing disulfide bond formation and VLP assembly.

It is another specific object of the invention to provide stable HPV capsomeres by expression of a DNA encoding a modified HPV L1 sequence wherein such modification comprises a carboxy deletion and/or at least one site specific mutation wherein such modification(s), upon expression, results in capsomeres that are substantially incapable of VLP assembly.

It is another specific object of the invention to provide modified HPV L1 nucleic acid sequences which upon expression result in stable HPV capsomeres that are substantially incapable of VLP assembly.

It is a more specific object of the invention to provide modified HPV L1 nucleic acid sequences which comprise a carboxy-terminal deletion and/or substitution or deletion modification involving at least one cysteine residue which upon expression results in capsomeres substantially incapable of VLP assembly.

It is another object of the invention to provide vaccines or diagnostic compositions containing stable HPV capsomeres produced by enzymatic, chemical, and/or recombinant methods.

It is still another object of the invention to use the stable HPV capsomeres of the present invention for the manufacture of neutralizing polyclonal and monoclonal antibodies.

It is another object of the invention to use the stable HPV capsomeres of the present invention as vaccines for conferring protection against HPV infection.

It is another object of the invention to use the stable HPV capsomeres of the present invention as diagnostic agents for detection of anti-HPV antibodies.

BRIEF DESCRIPTION OF THE INVENTION

Therefore, the invention generally relates to stable HPV capsomeres which present at least one virus-neutralizing conformational epitope expressed by an L1 protein expressed by a native (infectious) HPV, methods for their manufacture, and use thereof as diagnostic, prophylactic, and therapeutic agents.

As discussed in greater detail infra, it has been surprisingly discovered that HPV L1 proteins, which have been modified to favor capsomere formation, and substantially prevent the assembly of such capsomeres into VLPs, express conformational epitopes of native, infectious HPVs. In particular, they react with conformational antibodies produced against native, infectious HPVs and elicit the production of neutralizing antibodies.

These results are surprising given the significant adverse effects that even minor modifications to L1 proteins may incur. For example, it has been reported that a point mutation in the HPV-16 L1 protein disrupts assembly of the protein into virus-like particles and also impairs conformation, (Roden et al, *J. Virol.,* 68(11):1–5 (1994)).

Also, these capsomeres afford further advantages because they should result in highly homogeneous vaccine compositions. As the subject capsomeres, unlike non-modified L1 proteins, do not give rise to virus-like particles or other aggregates to any significant extent, compositions according to the invention should be substantially free of higher molecular weight forms of the L1 proteins. This is advantageous from a clinical standpoint wherein supplying a product of high consistency may be very important, indeed essential. Also, because capsomeres are significantly smaller than VLPs, they may be easier to purify on conventional chromatographic media, thereby increasing the ease of manufacture.

Definitions:

Major capsid protein or L1 protein

This refers to the structural protein of papillomavirus (PV) which constitutes the major portion of the PV capsid structure. This protein has reported application in the preparation of HPV vaccines and as a diagnostic agent.

Major capsid protein or L2 protein

This refers to the structural protein of papillomavirus which constitutes a minor portion of the PV viral capsid structure.

Virus-like particles or VLPs

This refers to the capsid-like structures which result upon expression and assembly of a papillomavirus L1 DNA sequence alone or in combination with an L2 DNA sequence. VLPs are morphologically and antigenically similar to authentic virions. VLPs may be produced in vivo, in suitable host cells, e.g., mammalian and insect host cells, or may form spontaneously upon purification of recombinant L1 proteins.

Capsomeres

This refers to an oligomeric configuration of the L1 protein which is constituted of L1 pentamers. Therefore, capsomeres comprise the "monomer" units which constitute the viral capsid structure.

Stable Capsomeres

This refers to capsomeres which are substantially incapable of assembly into virus-like particles. "Stable" in this context refers to the fact that these capsomeres substantially retain their capsomere morphology instead of assembling into VLPs. This is preferably accomplished by (i) removing enough of the carboxy-terminal portion of the L1 protein to prevent or substantially inhibit VLP assembly and/or (ii) preventing or substantially inhibiting disulfide bond formation. Disulfide bond formation may be prevented by elimination of one or more cysteine residues, e.g., by a substitution or deletion modification or by chemical means, e.g., by incubation and storage in sulfhydryl reducing agents, e.g., by reaction with β-mercaptoethanol, dithiothreitol, cysteine or other compounds which prevent oxidation of sulfhydryl groups. The free sulfhydryls on capsomeres generated by thiol reduction of VLPs are then "capped off", e.g., by reaction with alkylating agents, e.g., iodoacetamide or N-ethylmaleimide. The subject stable capsomeres will express at least one conformational neutralizing epitope expressed by the L1 protein of a corresponding native HPV virion.

Capsids

This refers to the structural portion of the papillomavirus which is comprised of capsomeres. More specifically, it is constituted of seventy-two capsomeres in a T=7 icosahedron structure.

Conformational L1 HPV Epitope

This refers to an epitope expressed on the surface of the subject stable papillomavirus capsomeres which is also expressed by an L1 protein of a corresponding native (wild-type), infectious HPV. It is well accepted by those skilled in the art that the presentation of conformational epitopes is essential to the efficacy (both as prophylactic and diagnostic agents) of HPV L1 protein immunogens.

Conformational Neutralizing L1 HPV Epitope

This refers to an epitope expressed on the surface of the subject stable papillomavirus capsomeres which is also expressed by an L1 protein of a corresponding native (wild-type), infectious HPV, and which elicits neutralizing antibodies. It is well accepted by those skilled in the art that the presentation of conformational neutralizing epitopes is essential to the efficacy (both as prophylactic and diagnostic agents) of HPV L1 protein immunogens.

Conformational Antibody

This refers to an antibody that specifically binds an epitope expressed by a naturally occurring (wild-type) HPV L1 protein, e.g., major capsid protein expressed on the surface of a native HPV.

Modified HPV L1 DNA

This refers to an HPV L1 DNA modified such that upon expression it results in an HPV L1 protein that presents at least one virus-neutralizing HPV L1 conformational epitope, and forms stable capsomeres that are substantially incapable of assembly into virus-like particles. "Substantially incapable" is relative to non-modified HPV L1 proteins which are known to spontaneously assembly into VLPs when expressed by suitable host cells, e.g., mammalian or insect cells, or in vitro during protein purification. Preferably, the modification will prevent VLP assembly altogether. However, the invention embraces modifications which substantially inhibit VLP formation, e.g., by at least 50%, more preferably by at least 90%, and most preferably by at least 95%. This can be determined by known methods, e.g., by visual detection of VLPs, e.g., by electron microscopy. The HPV L1 DNA may further comprise additional modification(s), e.g., additions, substitutions, deletions, provided that they do not adversely affect presentation of conformational neutralizing epitope(s). Preferably, modifications which prevent VLP assembly will comprise carboxy-terminal deletions and/or removal of at least one cysteine residue that inhibits or prevents VLP assembly.

Modification which inhibits disulfide bond formation

This refers to a modification of an HPV L1 DNA or corresponding protein which inhibits disulfide bond formation. Preferably, this is effected by deletion and/or substitution of at least one cysteine residue. However, such modifications also include the replacement of one or more amino acids, which are sufficiently proximate to a cysteine residue, e.g., to sterically hinder the cysteine residue and thereby prevent disulfide bond formation or interfere with capsomere-capsomere interactions. Alternatively, cysteine residues involved in VLP assembly can be chemically "capped-off", e.g., reaction with β-mercaptoethanol or dithiothreitol, followed by β-alkylation with iodoacetamide or N-ethylmaleimide. As discussed in greater detail infra, such cysteine residue(s) are comprised, in particular, in the carboxy-terminal portion of the protein, more specifically in the region of the L1 protein spanning amino acids 30 to 86, inclusive, relative to the carboxy terminal end of the L1 protein. In the specific case of HPV-11, a conserved cysteine is found at position 424 of the L1 protein, which apparently affects VLP assembly.

DETAILED DESCRIPTION OF FIGURES

Figure 1:
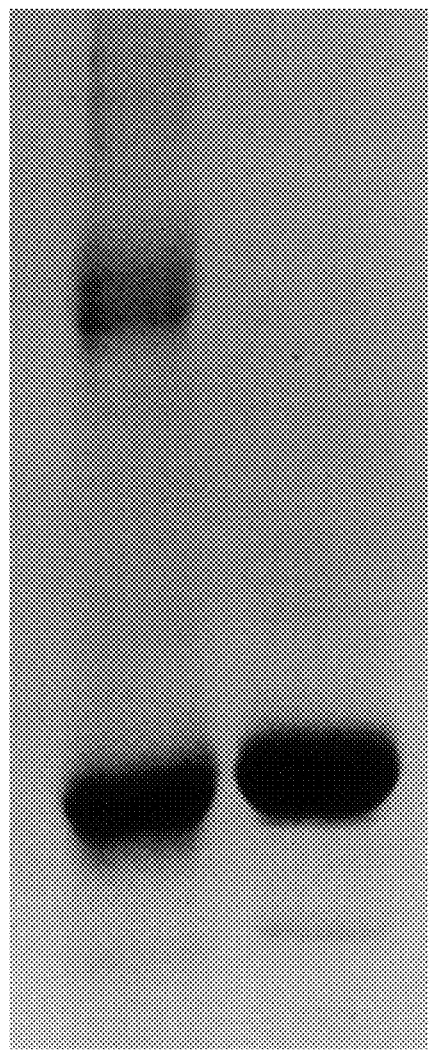

FIG. 1: SDS/PAGE analysis of purified HPV-11 L1 protein. The protein was mixed with sample preparation buffer in the absence (lane 1) or presence (lane 2) of 2 mM DTT and boiled for 2 minutes prior to gel electrophoresis. Shown on the left are the positions at which molecular weight standards (in $Da \times 10^{-3}$) migrated.

Figure 2:
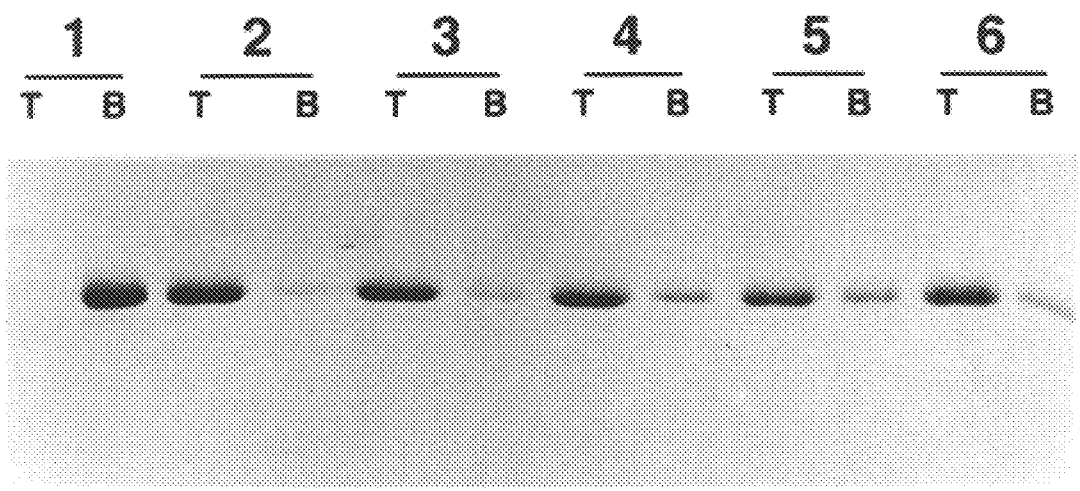

FIG. 2: 30% sucrose cushion analysis of HPV-11 VLP disassembly. HPV-11 preparations were treated at 4° C. as described in the text, and samples were taken at the top (T) or bottom (B) of the sucrose cushion prior to gel electrophoresis. Group 1, untreated, purified HPV-11 VLP starting material in PBS. Group 2, VLPs incubated with 5% βME for 16 hours. Group 3, VLPs incubated with 5% βME for 1 hour. Group 4, VLPs incubated with 2% βME for 16 hours. Group 5, VLPs incubated with 0.5% βME for 16 hours. Group 6, VLPs incubated with 10 mM DTT, 5 mM EDTA for 16 hours.

Figure 3:
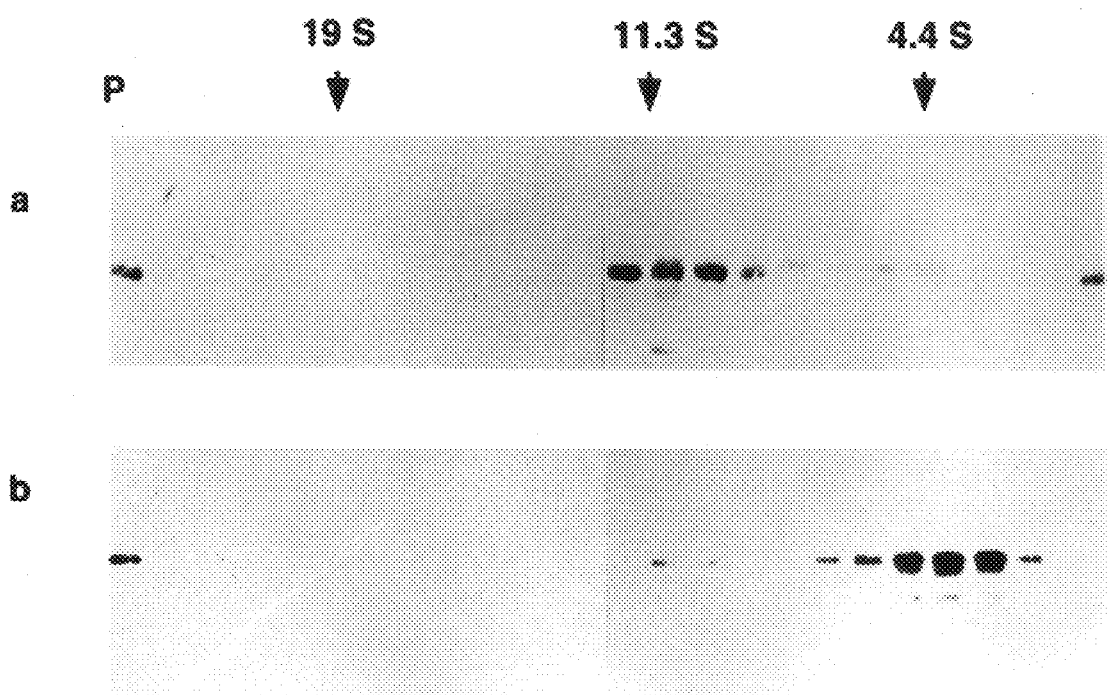

FIG. 3: 5–20% linear sucrose gradient analysis of disassembled HPV-11 VLPs. VLPs in PBS were incubated with 5% βME (a), or 200 mM $NaHCO_3$, pH 9.6 (b) for 16 hours at 4° C. and then centrifuged on a 5–20% linear sucrose gradient as described in the text. The gradient was collected in 25 fractions (0.5 ml), and the pellet (P) was resuspended in 0.5 ml PBS. Shown is an immunoblot demonstrating the position of the L1 protein across the gradient. Also indicated are the peak positions at which sedimentation standards migrated when run on separate gradients.

Figure 4:
Figure 4:
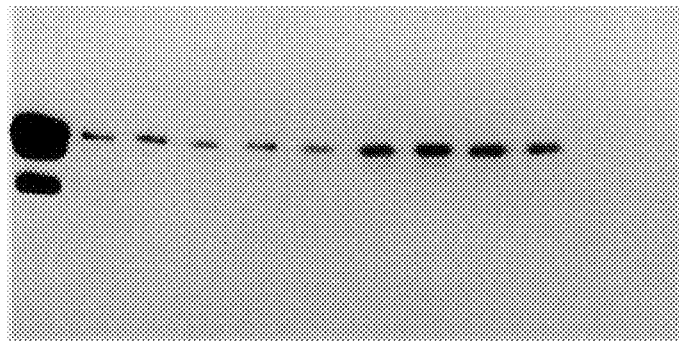
Figure 4:
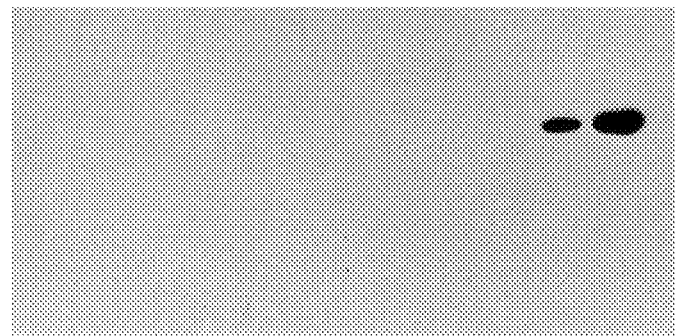
Figure 4:
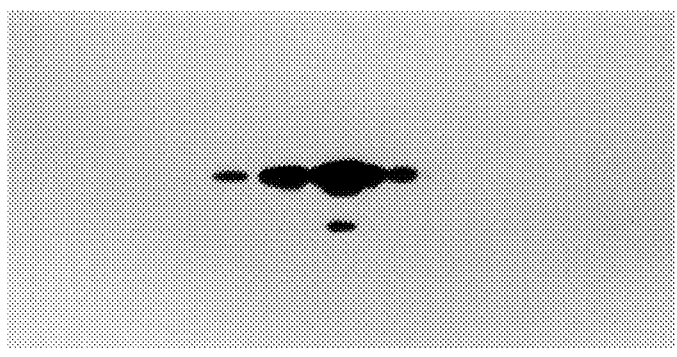

FIG. 4: 10–65% linear sucrose gradient analysis of HPV-11 VLPs in various states of assembly. An aliquot of purified VLP starting material (a) was incubated with 5% βME for 16 hours at 4° C.(b). A portion of βME-treated VLPs were then reassembled by dialysis into PBS-0.5 NaCl to remove reducing agent (c). The samples are then centrifuged on 10–65% linear sucrose gradients as described in the text. Each gradient was collected in 12 fractions (1 ml), and the pellet (P) was resuspended in 1 ml PBS. Shown are immunoblots demonstrating the positions at which the L1 protein migrated on the different gradients. Also indicated are the peak positions at which sedimentation standards migrated, as in FIG. 3.

FIG. 5: Electron micrographs of HPV-11 VLPs in various states of assembly. VLPs, treated as described, were stained with 2% phosphotungstic acid, applied to grids, and photographed at magnifications of 15–25,000 times. a, purified VLP starting material, b, VLPs disassembled to the level of capsomeres by incubation with 5% βME for 16 hours at 4° C. c, VLPs reassembled from disassembled VLPs by dialysis into PBS-0.5 NaCl, d, the central region of image c at greater magnification. Scale bar: a,c=200 nm; b,d,=100 nm.

FIG. 6: Reaction of intact and disassembled VLPs with HPV-11 structure-specific monoclonal antibodies. HPV-11 L1 VLP starting material (A), VLPs disassembled by treatment with 5% βME either without (B) or with (C) subsequent dialysis into PBS-0.5 M NaCl to remove reducing agent, and VLPs disassembled in the presence of 200 mM carbonate, pH 9.6 and then dialyzed into PBS-0.5 M NaCl (D) were attached to the wells of microtiter plates. HPV-11 structure-specific monoclonal antibodies H11.F1 (HPV-11 neutralizing; ▽) and H11.A3 (HPV-11 non-neutralizing; ●) were tested for immunoreactivity to the bound antigens in an ELISA as described in the Materials and Methods. Reactivity with monoclonal antibody AU1 (■), which recognizes a linear epitope found on HPV-11 L1, was used as a control to demonstrate antigen attachment to the microtiter wells.

Figure 7:
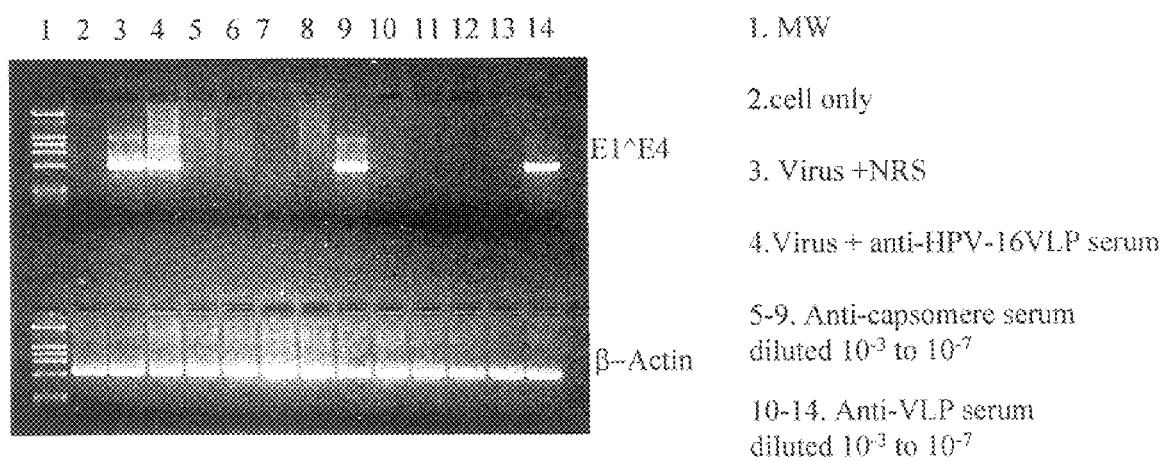

FIG. 7: Anti-HPV-11 capsid and anti-HPV-11 capsomere sera were incubated with HPV-11 virions for 75 min at 37° C. before addition to HaCaT cells. Alternatively, virions were added to cells without pre-incubation with serum, or virions were pre-incubated with pre-immune serum prior to infection of HaCaT cells. Six day post-infection, the cells were harvested and total RNA was extracted. Ten percent of the total RNA was used for cDNA synthesis with an oligo d-T primer. Ten percent of the cDNA was then used as template for nested PCR using primers specific for the HPV-11 El^E4 spliced message. PCR products were separated on 2% agarose gels. Gels were stained with ethidium bromide and examined under UV light for the presence of the 0.6 kb El^E4 band (top). PCR amplification of β-actin was performed on all cDNA samples as an internal control (bottom). The expected size of the β-actin band is 0.6 kb. Lane A contains molecular size markers. Lanes B and C contain PCR products obtained with RNA isolated from cells infected with HPV-11 pre-incubated with a $10^{-2}$ dilution of normal rabbit serum. The ability to detect the El^E4 PCR product indicates that virus is not neutralized by this control serum. Lanes D and E represent reactions carried out with RNA from cells incubated with virus that had not been pre-incubated with serum, and lane F and G are from cells incubated without virus. As expected, the El^E4 band is detected in virus-infected but not in uninfected cells. Lanes H–L contain PCR products from cells infected with virus that had been pre-incubated with serial $\log_{10}$ dilutions of anti-HPV-11 capsid antiserum ($10^{-3}$–$10^{-7}$). This antiserum neutralizes the virus at all dilutions tested. Lanes M–Q show PCR products obtained when cells were infected with virus preincubated with serial $\log_{10}$ dilutions of anti-HPV-11 capsomere serum ($10^{-3}$–$10^{-7}$). This antiserum effectively neutralizes the virus out to a $10^{-6}$ dilution.

DETAILED DESCRIPTION OF THE INVENTION

As discussed, the present invention generally relates to stable HPV capsomeres which present at least one virus-neutralizing conformational epitope of a native (infectious) HPV, which are substantially incapable of assembly into VLPs (when subjected to conditions that normally result in VLP assembly)

The present invention was based, in part, on observations made by the inventors during quantitative disassembly and reassembly of HPV-11 VLPs in vitro. Specifically, it was observed that maximal VLP disassembly required prolonged exposure to very high concentrations of reducing agent. This suggested that stabilizing disulfide bonds are buried and inaccessible, and that exposure of these bonds to solvent by local fluctuations is very infrequent.

However, this observation conflicted to some extent with other reported experiments which suggested that residues in the C-terminal end of the L1 protein may be important to capsomere formation which is a portion of the L1 molecule which would have been predicted to be relatively accessible to solvent. Specifically, it was reported that the BPV L1 protein which contained a relatively small carboxy-terminal deletion (24 carbon-terminal amino acids removed) still assembled into VLPs. By contrast, a BPV-1 L1 protein containing a larger carboxy deletion (44 amino acids) exhibited significantly inhibited ability to form capsids (Paintsil et al, *Virology*, 223:238–244 (1996)). Moreover, it was recently reported that an HPV-1 protein containing an even larger C-terminal deletion (86 amino acids) yielded capsomeres apparently incapable of forming capsid-like structures. (Li et al, *J. Virol.*, 71:2988–2995 (1997)). These results suggested the importance of C-terminal residues in VLP formation.

In this regard, it has been reported that in the 3.8 Å structure of the SV40 virus, that the C-terminal domain of the VP1 protein is involved in the formation of intra-capsomeric bonds which stabilize the capsid, by extending across the space between capsomeres and forming part of the extended β-sheet of the neighboring capsomeric L1 protein. However, the requirement of disulfide bonds for this interaction was not resolved in the crystal structure because of disorder in this portion of the molecule (Liddington et al, *Nature*, 354:278–284 (1991)). Also, it was previously reported that 15 Å strands connecting capsomeres can be seen, at low resolution, in the cryoelectron microscopic reconstruction of the BPV structure (Baker et al, *Biophys J.*, 60:1445–1456 (1991); Belnap et al, *J. Mol. Biol.*, 259:249–263 (1996)); and also in negatively-stained HPV virions (Yabe et al, *Virology*, 227:13–23 (1997)). These results suggested that linker arms may stabilize papillomavirudae capsids. [However, it is noted that these references did not provide any information concerning what specific residues or role of other factors which potentially could have affected PV capsid formation and stability.]

The present invention was further based on experiments which demonstrated that capsomeres generated from HPV-11 VLPs, even after long exposure to high concentration of reducing agent, still retain structural epitopes found on native VLPs (disclosed infra in the Examples). This was demonstrated in part based on their reactivity with a panel of antibodies that specifically react with HPV-11 L1 VLPs but do not with "denatured" L1 proteins. These results were surprising as it had previously been reported that the binding of two of the tested antibodies was VLP-dependent. (Ludmeyer et al, *J. Virol.*, 71:3834–3837 (1997)). Also, it was demonstrated (also disclosed infra) that HPV-11 capsomeres are capable of eliciting the production of virus-neutralizing antibodies (also disclosed infra in Example 6). Therefore, these results and observations in combination suggested to the inventors the suitability of stable HPV capsomeres as immunogens for conferring protection against HPV infection.

As discussed, given their resistance to VLP formation, the stable capsomeres potentially will give rise to vaccines of enhanced homogeneity. Also, HPV capsomeres, because of their smaller size and molecular weight relative to VLPs, should be easier to purify then VLPs, thereby facilitating vaccine manufacture.

More specifically, these results, most especially the fact that capsomere formation was favored by very high reducing agent, suggested that one or more cysteine residues are likely involved in VLP assembly and disassembly. Moreover, the fact that deletions in the carboxy terminal portion of the L1 protein inhibits (or prevents) VLP assembly further suggested that at least one cysteine residue involved in VLP assembly is apparently comprised in the carboxy-terminal portion of the L1 protein.

In general, stable capsomeres will be produced by one of two general methods. The first method comprises expression of a modified HPV L1 DNA which contains at least one modification(s) such that upon expression it results in the production of stable capsomere. This first method comprises the following steps:

(i) obtaining a desired HPV L1 DNA sequence;

(ii) introducing suitable modification(s) therein by deletion and/or site-specific mutagenesis that prevent VLP assembly and result in stable capsomere upon expression;

(iii) expressing said modified HPV L1 DNA in suitable host cells, and (iv) recovering capsomere from said host cells.

The second method comprises expression of a non-modified HPV L1 protein, and modifying the resultant expression product to produce stable capsomere. Specifically, the second method will comprise the following steps:

(i) obtaining a desired HPV L1 DNA;

(ii) expressing said HPV L1 DNA in suitable host cells;

(iii) purifying the resultant VLPs under conditions (e.g. high reducing agent concentration) that provide for the dissociation of said VLPs into capsomere and chemically "capping off" to prevent VLP reassembly, e.g., by alkylating free sulfhydryls; or (iv) purifying the resultant VLPs or capsomere produced upon expression of the HPV L1 DNA during step (ii) and digesting said VLPs or capsomeres with a protease (e.g. trypsin) under conditions that result in stable capsomere wherein a sufficient amount of the carboxy-terminal portion of the L1 protein has been removed which is required for VLP assembly.

Many HPV L1 DNAs have been reported in the literature and are publicly available. (See, e.g., Baker, Sequence Analysis of Papillomavirus, *Genomes*, pp. 321–384; Long et al, U.S. Pat. No. 5,437,931, Cole et al, *J. Mol Biol.*, 193:599–608 (1987); Danos et al, *EMBO J.*, 1:231–236 (1982); Cole et al *J. Virol.*, 38(3):991–995 (1986).) Also, it is well known that HPV L1 DNAs exhibit significant homology. Therefore, a desired HPV L1 DNA can easily be obtained, e.g., by the use of a previously reported HPV L1 DNA or a fragment thereof as a hybridization probe or as a primer during polymerization chain reaction (PCR) amplification. Indeed, numerous HPV L1 DNAs have been cloned and expressed.

Preferably, the HPV L1 DNA said in the subject invention will be derived from an HPV which is involved in cancer or condyloma acuminata, e.g., HPV-16, HPV-18, HPV-31, HPV-33, HPV-35, HPV-39, HPV-45, HPV-51, HPV-52, and HPV-56 are involved in cancer, and HPV-6, HPV-11, HPV-30, HPV-42, HPV-43, HPV-44, HPV-54, HPV-55, and HPV-70, are involved in warts. However, the subject stable capsomeres may be produced from any desired HPV L1 DNA.

According to the first embodiment of the invention, the selected HPV L1 DNA will be modified such that the modified L1 DNA upon expression results in stable capsomeres which do not significantly assemble into larger oligomers such as VLPs and which present at least one virus-neutralizing conformational epitope of a native, infectious HPV. This will be effected by introducing one or both of the following modifications:

(i) deletion of up to 86 carboxy-terminal residues, and more preferably deletion of from about 30 to 86 carboxy-terminal residues inclusive; and (ii) introducing one or more site specific modifications which inhibit or prevent disulfide bond formation, in particular disulfide bond(s) which are involved in VLP assembly. It is noted that if the L1 protein contains modifications that prevent or inhibit disulfide bond formation, it may not be necessary to delete carboxy-terminal amino acids to generate stable capsomers.

Methods for introducing desired deletions in DNA sequences are well known in the art. For example, carboxy-terminal deletions can be introduced by cleaving the L1 DNA with appropriate restriction enzyme(s). Alternatively, L1 deletions can be constructed by PCR mutagenesis of the L1 gene such as described by Paintsil et al (*Virology*, 223:238–244 (1996)). Still alternatively, an HPV L1 DNA containing a deletion in the carboxy-terminal end of the L1 gene can be made by DNA synthesis.

Similarly, methods for introducing desired site specific mutations in DNA sequences are well known. Preferably, the selected HPV L1 DNA will be mutagenized by removal of at least one cysteine residue involved in VLP assembly. As discussed, this can be accomplished by a substitution modification, i.e., substituting a selected cysteine codon with another codon, or by deletion. Substitution mutations are preferred as this may reduce the potential of adversely affecting the three-dimensional structure of the resultant protein and the presentation of desired conformational epitopes. Especially preferred cysteine residues targeted for modification are those at the carboxy-terminal portion of the protein, most especially those contained within carboxy-terminal 86 amino acids of the L1 protein. However, other cysteine residues may also potentially be modified provided that they do not impair capsomere production and presentation of conformational epitopes upon expression. Suitable methods for introducing mutations in PV L1 DNAs are also disclosed in Paintsil et al (Id.). In the specific case of HPV-11, a cysteine residue targeted for modification is found at position 424.

Alternatively, disulfide bond formation may be prevented by modification of residues proximate to cysteine residues, e.g., by introduction of amino acids which sterically hinder disulfide bond formation or interfere with capsomere-capsomere interactions.

While stable capsomeres should result from either of these modifications alone, the introduction of both carboxy deletions and cysteine residue modifications into an HPV-L1 sequence may impart synergistic effects. Moreover, as noted in this embodiment of the invention, the deletion of fewer than 86 carboxy-terminal amino acids may be effected, thereby potentially retaining conformational epitopes that may be present in this portion of the L1 protein. These modified or non-modified L1 DNA will then be expressed in a selected expression system.

The selected host and expression vector will be cultured under conditions that favor the production of the subject stable HPV capsomeres. This will largely depend upon the selected host system and regulatory sequences contained in the vector, e.g., whether expression requires induction. After expression, the HPV capsomeres will be recovered from the host cells. The means of recovery will also depend to some extent on the host/vector system.

For example, if an intracellular expression vector is selected, the host cells will need to be lysed and the HPV capsomeres recovered from the lysate. By contrast, if the expression vector contains sequences that facilitate secretion, HPV capsomeres can be recovered directly from the culture medium. Methods for recovery of heterologous proteins from recombinant host cells and culture medium are well known in the art.

The subject modified HPV L1 sequences may be expressed in any host cell that provides for the expression of recoverable yields of HPV capsomeres. Suitable host systems for expression of recombinant proteins are well known and include, by way of example, bacteria, mammalian cells, yeast, and insect cells. A preferred expression system comprises the baculovirus/insect cell system used in the examples as this system provides for high protein yields. However, HPV L1 proteins can be produced in other systems, in particular bacteria and yeast.

Suitable vectors for cloning of expression of the subject HPV L1 encoding DNA sequences are well known in the art and commercially available. Further, suitable regulatory sequences for achieving cloning and expression, e.g., promoters, polyadenylation sequences, enhancers, selectable markers are also well known. The selection of appropriate sequences for obtaining recoverable protein yields is routine to one skilled in the art.

As discussed, when expressing the subject modified HPV L1 DNAs, the host cells should only express HPV L1 protein in the form of HPV capsomeres (as the L1 sequence has been modified to prevent VLP assembly). However, as discussed, the present invention further embraces the expression of non-modified HPV L1 DNAs, and the use of the resultant expression product to produce stable HPV capsomeres.

This aspect of the invention will preferably be conducted by expression of non-modified HPV L1 DNAs in a selected host/vector system, recovery of resultant HPV VLPs, and the conversion of said VLPs into stable capsomeres. It is well known that non-modified HPV L1 DNAs upon expression in eukaryotic cells may spontaneously assemble into VLPs, or in the case of cells wherein assembly does not occur in vivo (bacterial cells) this may occur during purification.

While VLPs have reported application in HPV vaccines and diagnostics, the object of the present invention is to produce stable capsomeres, as it has been discovered that they present conformational neutralizing epitopes and induce neutralizing antisera.

This can be accomplished, e.g., by enzymatic treatment of the HPV VLPs with an appropriate enzyme, e.g., trypsin, under conditions that remove the carboxy-terminal portion of the HPV VLPs. In the specific case of HPV-11 VLPs, proteotype digestion with trypsin has been reported to remove the 86 terminal amino acids. (Li et al, *J. Virol* 71:2988–2995 (1997)). Moreover, said limited proteolytic digestion of purified HPV-11 VLPs results in a homogeneous population of stable HPV capsomeres, i.e., which are resistant to VLP assembly. (Li et al, *J. Virol.*, 71:2988–2995 (1997)).

Alternatively, the expressed HPV L1 proteins can be disassembled during the course of HPV capsomere purification. This can be effected by, e.g., conducting all the purification steps in the presence of high concentration of reducing agent, e.g., on the order of 1% to 5% by weight of reducing agent, e.g., β-mercaptoethanol. This is discussed in greater detail in the Examples.

Reactive sulfhydryls on the purified capsomeres can be chemically "capped-off", thereby preventing disulfide bond formation (between cysteine residues on different capsomeres) by reaction of cysteine residues with alkylating agents, such as iodoacetamide after reduction.

As discussed, the present invention should be broadly applicable to any HPV L1 sequence. There are a variety of PV types known in the art. Further, particular types of PVs are associated with particular infections such as flat warts, cutaneous warts, epidermodysplasia verruciformis, lesions and cervical cancer. Over 60 different HPV types have been identified in clinical lesions by viral nucleotide sequence homology studies. See, for example, Jenson et al, "Human papillomaviruses" In: Belshe, R. ed., Textbook of human virology, Second Edition, MASS:PSG, 1989:951 and Kremsdorf et al, *J. Virol.*, 52:1013–1018 (1984). The HPV type determines, in part, the site of infection, the pathological features and clinical appearance as well as the clinical course of the respective lesion.

Because it is believed that there is little or no cross-immunity for HPV types and immunity to infection is HPV type-specific, it will be necessary to produce recombinant HPV capsomere for each specific HPV type upon which protection or treatment is needed. However, due to the homology between the L1 proteins and genes, hybridization techniques can be utilized to isolate the particular L1 gene of interest. Nucleotide probes selected from regions of the L1 protein which have been demonstrated to show sequence homology, can be utilized to isolate other L1 genes. Methods for hybridization are known in the art. See, for example, *Nucleic Acid Hybridization, A Practical Approach*, IRL Press, Washington, D.C. (1985); *Molecular Cloning, A Laboratory Manual*, Maniatis et al, eds., Cold Spring Harbor Laboratory, Cold Spring Harbor, N.Y. (1982); and *Molecular Cloning, A Laboratory Manual*, Sambrook et al, eds., Cold Spring Harbor Laboratory, Second Edition, Cold Spring Harbor, N.Y. (1989). Alternatively, PCR methods can be utilized to amplify L1 genes or gene fragments. See, for example, U.S. Pat. Nos. 4,683,195; 4,683,202; and 4,800, 159.

Virus particles can also be isolated for a particular papillomavirus type, the DNA cloned, and the nucleic acid sequences encoding L1 proteins isolated. Methods for isolation of viral particles and cloning of virus DNAs have been reported. See, for example, Heilman et al. *J. Virology*, 36:395–407 (1980); Beaudenon et al, *Nature*, 321:246–249 (1986); Georges et al, *J. Virology*, 51:530–538 (1984); Kremsdorf et al, *J. Virology*, 52:1013–1018 (1984); Clad et al, *Virology*, 118:254–259 (1982); DeVilliers et al, *J. Virology*, 40:932–935 (1981); and European Patent Application 0133123.

Alternatively, the L1 protein for a particular human papillomavirus can be isolated, the amino acid sequence determined and nucleic acid probes constructed based on the predicted DNA sequence. Such probes can be utilized in isolating the L1 gene from a library of the papillomavirus DNA. See, for example, Suggs et al, *PNAS,* 78(11):6613–6617 (1981). See also, Young and Davis, *PNAS,* 80:1194 (1983).

Since the HPV capsomere must express at least one neutralizing conformational epitope expressed by an intact, infectious HPV, the particular expression system is important to the invention. An expression system must be utilized which provides for the production of capsomeres having appropriate conformation. Such expression systems should desirably also produce high levels of capsomere. Generally, the expression system will comprise a vector having the L1 protein of interest and the appropriate regulatory regions as well as a suitable host cell.

As discussed, baculovirus vectors are preferably utilized. A baculovirus system offers the advantage that a large percentage of cells can be induced to express protein due to the use of infection rather than transfection techniques. While baculovirus is an insect virus and grows in insect cells (SF9), these cells retain many of the eucaryotic mechanisms for processing of proteins including glycosylation and phosphorylation which may be important for generating proteins of appropriate conformation. Baculovirus vector systems are known in the art. See, for example, Summers and Smith, Texas Agricultural Experimental Bulletin No. 1555 (1987); Smith et al, *Mol. Cell Biol.,* 3:2156–2165 (1985); Posse, *Virus Research,* 5:4359 (1986); and Matsuura, *J. Gen. Virol.,* 68:1233–1250 (1987). Also, it has been reported that baculovirus/infected cells express HPV L1 proteins exhibiting appropriate conformation.

For expression in an appropriate expression system, an L1 gene or modified L1 gene is operably linked into an expression vector and introduced into a host cell to enable the expression of the L1 protein by that cell. The gene with the appropriate regulatory regions will be provided in proper orientation and reading frame to allow for expression. Methods for gene construction are known in the art. See, in particular, *Molecular Cloning, A Laboratory Manual,* Sambrook et al, eds., Cold Spring Harbor Laboratory, Second Edition, Cold Spring Harbor, N.Y. (1989) and the references cited therein.

A wide variety of transcriptional and regulatory sequences may be employed. The signals may be derived from viral sources, where the regulatory signals are associated with a particular gene which has a high level of expression. That is, strong promoters, for example, of viral or mammalian sources, will be utilized. In this manner, the optimum conditions for carrying our the invention include the cloning of the L1 gene into an expression vector that will overexpress conformationally-dependent virus-neutralizing epitopes of the L1 protein in transfected or infected target cells.

The suitability of the particular stable HPV capsomeres produced according to the invention as vaccines or as diagnostic agents is confirmed by reaction with antibodies or monoclonal antibodies which react or recognize conformational epitopes present on the intact virion and based on their ability to elicit the production of neutralizing antiserum. Suitable assays determining whether neutralizing antibodies are produced are known to those skilled in the art. Further, this application teaches (in Example 6) an in vitro assay suitable for determining whether the HPV capsomere elicits neutralizing antibodies. This is an essential characteristic of HPV capsomeres which are to be used in HPV vaccines. In this manner, it can be verified whether the HPV capsomeres will confer protection against HPV infection. Thus, other expression vectors and expression systems can be tested for use in the invention.

As discussed, the capsomeres of the present invention can be utilized to detect, diagnose, serotype, and treat papillomavirus infection. When used for diagnosis or serotyping, capsomeres according to the invention may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^3$H, 125I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, and $^{109}$Pd.

Examples of suitable fluorescent labels include a $^{152}$Eu label, a fluorescein label, an isothiocyanate label, a rhodamine label, a phycoerythrin label, a phycocyanin label, and allophycocyanin label, an o-phthaldehyde label, an fluorescamine label, etc.

Examples of suitable toxin labels include diphtheria toxin, ricin, and cholera toxin. Examples of chemiluminescent labels include a luminal label, an isoluminal label, an aromatic acridinium ester label, and imidazole label, and acridinium salt label, an oxalate ester label, a luciferin label, a luciferase label, an aequorin label, etc.

Those of ordinary skill in the art will know of other suitable labels which may be employed in accordance with the present invention. The binding of these labels to consomers can be accomplished using standard techniques commonly known to those of ordinary skill in the art. Typical techniques are described by Kennedy, J. H., et al, *Clin. Chim. Acta,* 70:1–31 (1976), and Schurs, A. H. W. M., et al, *Clin. Chim. Acta,* 81:1–40 (1977). Coupling techniques mentioned in the latter are the glutaraldehyde method, the periodate method, the dimaleimide method, the m-maleimido-benzyl-N-hydroxy-succinimide ester method, all these methods incorporated by reference herein.

The detection of the anti-HPV antibodies using the subject capsomere can be improved through the use of carriers. Well-known carriers include glass, polystyrene, polypropylene, polyethylene, dextran, nylon, amylases, natural and modified celluloses, polyacrylamides, agaroses and magnetite. The nature of the carrier can be either soluble to some extent or insoluble for the purposes of the present invention. Those skilled in the art will note many other carriers suitable for binding proteins, or will be able to ascertain the same by use of routine experimentation.

The most important aspect of the present invention, however, involves the development of PV type-specific vaccines. The vaccines of the invention will contain an amount of the subject stable HPV capsomeres sufficient to induce formation of neutralizing antibodies in the host contained in a pharmaceutically acceptable carrier.

Administration of the subject capsomere containing vaccines may be effected by any pharmaceutically acceptable means, e.g., parenterally, locally or systemically, including by way of example, oral, intranasal, intravenous, intramuscular, and topical administration. The manner of administration depends on factors including the natural route of infection. The dosage administered will depend upon factors including the age, health, weight, kind of concurrent treatment, if any, and nature and type of the particular human papillomavirus. The vaccine may be employed in dosage form such as capsules, liquid solutions, suspensions, or elixirs, for oral administration, or sterile liquid formulations such as solutions or suspensions for parenteral or intranasal use. An inert, immunologically acceptable carrier is preferably used, such as saline or phosphate-buffered saline.

The vaccines will be administered in therapeutically effective amounts. That is, in amounts sufficient to produce a protective immunological response. Generally, the vaccines will be administered in dosages ranging from about 0.1 mg protein to about 20 mg protein, more generally about 0.001 mg to about 100 mg protein. A single or multiple dosages can be administered.

The method of the present invention makes possible the preparation of HPV capsomere containing vaccines for preventing papillomavirus infection. Further, by following the methods of the invention, vaccines for any immunogenic type of human specific papillomavirus can be made.

As more than one PV type may be associated with PV infections, the vaccines may comprise stable HPV capsomeres derived from more than one type of PV. For example, as HPV 16 and 18 are associated with cervical carcinomas, therefore a vaccine for cervical neoplasia may comprise capsomere of HPV 16; of HPV 18; or both HPV 16 and 18.

In fact, a variety of neoplasia are known to be associated with PV infections. For example, HPVs 3a and 10 have been associated with flat warts. A number of HPV types have been reported to be associated with epidermodysplasia verruciformis (EV) including HPVs 3a, 5, 8, 9, 10, and 12. HPVs 1, 2, 4, and 7 have been reported to be associated with cutaneous warts and HPVs 6b, 11a, 13, and 16 are associated with lesions of the mucus membranes. See, for example, Kremsdorf et al, *J. Virol.*, 52:1013–1018 (1984); Beaudenon et al, *Nature*, 321:246–249 (1986); Heilman et al, *J. Virol.*, 36:395–407 (1980); and DeVilliers et al, *J. Virol.*, 40:932–935 (1981). Thus, the subject vaccine formulations may comprise a mixture of capsomere from different HPV types depending upon the desired protection.

As indicated, the HPV capsomeres of the invention can also be utilized for serotyping and for incorporation in serotyping kits.

For serological testing, the kits will comprise the subject HPV capsomere and means for detection such as enzyme substrates, labelled antibody, and the like.

Having now generally described the invention, the following examples are offered by way of illustration and not intended to be limiting unless otherwise specified.

EXAMPLES

The following materials and methods were used in the Examples.

Chemicals

The anti-HPV mouse monoclonal antibody AU1 was purchased from Berkely Antibody Co., monoclonal antibodies H11.F1 and H11.A3 were purchased from Pennsylvania State University (Christensen et al., 1990), horseradish peroxidase (HRP)-labelled goat anti-mouse IgG was purchased either from Southern Biotechnology Associates, Inc. or Gibco/BRL, 10× phosphate-buffered saline (PBS) minus $Ca^{2+}$ or $Mg^{2+}$ was from Gibco/BRL, ECL reagents were purchased from Amersham, protein molecular weight standards were purchased from BioRad, and formvar/carbon-coated copper grids and phosphotungstic acid were purchased from Electron Microscopy Sciences. All other reagents were purchased from Sigma.

HPV-11 VLPs

HPV-11 L1 proteins were heterologously expressed in *Trichoplusia ni* (High Five®) cells infected with recombinant baculovirus encoding the complete L1 open reading frame downstream of the polyhedron promoter as described (Ghim et al, *Immunology of Human Papillomaviruses*, Plenum, N.Y., pp 147–152 (1994). Cells were harvested approximately 72 hours post-infection, pelleted by centrifugation, and frozen. For preparation of VLPs (all steps performed at 4° C.), the cell paste was resuspended in homogenization buffer (20 mM $NaH_2PO_4$, 150 mM NaCl, pH 7.4, containing 10 mg/ml leupeptin, 1 mg/ml aprotinin, and 1 mg/ml pepstatin A) and lysed at ~3,000 PSI in a microfluidizer (Microfluidics model HC8000/3A). The homogenized lysate was then centrifuged at 100,000× g for 90 minutes, and the supernatant removed. The pellet, containing HPV-11 VLPs, was resuspended in PBS containing CsCl (405 g/L) and centrifuged at 66,000× g for 90 minutes to remove a contaminating buoyant layer. The clarified lysate was then centrifuged overnight at 83,000× g in a vertical rotor, and the VLP band was collected (at a density of 1.28 $g/cm^3$). The VLPs were diluted >2-fold in PBS-0.5M NaCl, to reduce the density of the solution, and layered over a two component step gradient composed of 30% and 63% sucrose (w/w in PBS-0.5M NaCl). The gradients were centrifuged at 167,000× g for 3 hours in a vertical rotor, and the purified VLP band was collected at the interface between the 30% and 63% sucrose solutions. The VLPs were then dialyzed into selected buffers (either PBS, or PBS with NaCl added to a final concentration of 0.3 M or 0.5 M), and stored at 4° C. Protein concentration was determined by the Bradford assay (Bradford, 1976) using bovine serum albumin as the reference protein, and L1 content was determined as described by Suzich et al., *Proc. Natl. Acad. Sci. USA*, 92:11553–11557 (1995). Starting with 25–30 g of wet cell paste, the above protocol yielded 15–25 mg of HPV-11 VLPs.

Sucrose gradient centrifugation

Three types of sucrose gradients were used in these experiments. First, centrifugation on 30% sucrose cushions was used to identify conditions which favored the disassembly of VLPs into smaller, soluble components. 100–200 µl reaction mixtures containing VLPs (50–100 µg total protein) plus or minus potential disrupting agents were layered atop 5 ml centrifuge tubes filled with 4.8 ml of 30% sucrose (w/w in PBS-0.5M NaCl) and centrifuged at 197,000× g for 2 hours at 4° C. in a swinging bucket rotor. A 50 µl aliquot was taken from the very top of the tube, and mixed with 2× Laemmli sample preparation buffer (Laemmli, *Nature*, 227:680–685 (1970). The remainder of the 30% sucrose cushion was removed by pipet, and the "pellet" (typically none was visible) was resuspended in 100 µl of 1× Laemmli sample preparation buffer. The presence of HPV-11 L1 protein at the top or bottom of the 30% sucrose cushion was then determined by SDS/PAGE, and the relative amount of L1 quantified by analysis of digitized gels. Second, the state of disassembled VLPs was determined by rate-zonal centrifugation through 5–20% linear sucrose gradients. Disassembled VLPs (100–200 µg total protein in 400 ml) were layered atop preformed 11.6 ml gradients composed of 5–20% sucrose (w/v in PBS-0.5M NaCl), and centrifuged at 111,000× g for 24 hours at 4° C. in a swinging bucket rotor. Fractions (0.5 ml) were collected across the gradient, and the "pellet" (typically none was visible) was resuspended in 0.5 ml of PBS by dounce homogenization. The position of HPV-11 L1 protein across the gradient was determined by immunoblotting. The gradients were calibrated using standard proteins with established sedimentation coefficients (*E. coli* β-galactosidase, 19 S; catalase, 11.3 S; bovine serum albumin, 4.3 S), and the percentage of sucrose in the fractions was determined by refractometry.

Third, the state of initial, disassembled, and reassembled VLPs was determined by rate-zonal centrifugation through 10–65% linear sucrose gradients. HPV-11 L1 protein (100–200 μg total protein in 400 μl) in various states of assembly was layered atop preformed 11.6 ml gradients composed of 10–65% sucrose (w/v in PBS-0.5M NaCl), and centrifuged at 188,000× g for 2.5 hours at 4° C. in a swinging bucket rotor. The gradients were collected (in 1.0 ml fractions), analyzed, and calibrated as above, with parvovirus B19 (70 S) and HPV-18 L1 VLPs (160 S) used as additional calibration standards.

Gel Electrophoresis

SDS/PAGE SDS/PAGE was performed largely according to the method of Laemmli, *Nature*, 227:680–685 (1970). Samples were mixed with sample preparation buffer, boiled for 2 minutes, briefly spun in a minifuge, and loaded onto 7.5% (FIG. 1) or 10% (FIGS. 2–4) minigels with a 4% stacking gel. Gels were run for approximately 1 hour at 20 mA constant current at room temperature, and protein was visualized by staining with Coomassie brilliant blue R250.

Immunoblotting

Electroblots of HPV-11 L1 from SDS/PAGE gels were prepared largely according to the method of Towbin et al., *Proc. Natl. Acad. Sci. USA*, 76:4350–4354 (1979). The blots were blocked with 1% nonfat milk protein in PBS overnight at 4° C. The blots were probed with AU1, a mouse monoclonal directed against a linear epitope on papillomavirus L1 proteins (Lim et al., *J. Infect. Dis.*, 162:1263–1269 (1990) for 90 minutes, washed with PBS, 0.1% Tween-80, and then reblocked for 30 minutes. The blots were then incubated with HRP-labeled goat anti-mouse IgG (Southern Biotechnology Associates, Inc.) for 40 minutes, and washed as above. The blots were then developed with ECL Western blotting reagent, and exposed to X-ray film.

Analysis of gels

The $M_r$ of monomeric and oligomeric L1 were determined from their $R_f$ values on 7.5% SDS/PAGE, in comparison to standard proteins (See and Jackowski, In T. E. Creighton (ed) *Protein structure: a practical approach*, IRL Press, NY, pp 1–21, (1989). When indicated, gels and immunoblots were digitized on a Hewlett Packard Scanjet Plus flatbed densitometer, and the relative intensity of bands was determined using Scan Analysis software (Version 2.2; Specom Research).

Electron microscopy

Protein samples were allowed to settle on formvar and carbon-coated copper grids, blotted dry, and stained with freshly-filtered 2% phosphotungstic acid (pH 6.8). Grids were examined in a JEOL model 1005 transmission electron microscope at an accelerating voltage of 100 KV and photographed at nominal magnifications of 15–25,000×.

Enzyme-linked immunosorbent assay (ELISA)

HPV-11 L1 VLPs (0.5–1.0 mg/ml L1) in PBS-0.3 M NaCl were either stored without treatment at 4° C., or incubated overnight at 4° C. following addition of βME (to a final concentration of 5%) or 2.0 M carbonate buffer, pH 9.6 (to a final concentration of 200 mM carbonate). A portion of the treated samples were then dialyzed against 4×1L PBS-0.5 M NaCl at 4° C. for about 24 hrs. All samples were diluted to a concentration of 0.8 μg L1/ml and distributed into the wells of microtiter plates (80 ng L1 per well). Untreated VLPs and dialyzed material were diluted into PBS. Sample treated with βME without subsequent dialysis was diluted into PBS containing 5% βME, and undialyzed sample incubated in 200 mM carbonate was diluted into 200 mM carbonate, pH 9.6. Following incubation at 37° C. for 1 hr, the plates were washed with PBS containing 0.1% Tween 20 (PBS-Tw) and blocked with 5% nonfat milk protein in PBS. Monoclonal antibodies were diluted in 1% nonfat milk in PBS and added to the wells. Following a 1 hr incubation at room temperature, the plates were washed with PBS-Tw and HRP-labeled goat anti-mouse IgG (Gibco/BRL) was added. After 1 hr at room temperature, the plates were washed as above and developed with HRP substrate. Optical density measurements were made at 405 nm at the 15 min end-point. Averages of duplicate wells were calculated as the final optical density values.

Example 1

Quantitative disassembly of HPV-11 VLPs

Figure 5A:
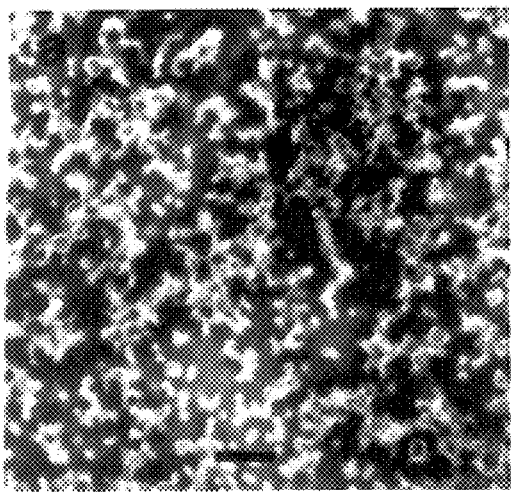
Figure 5C:
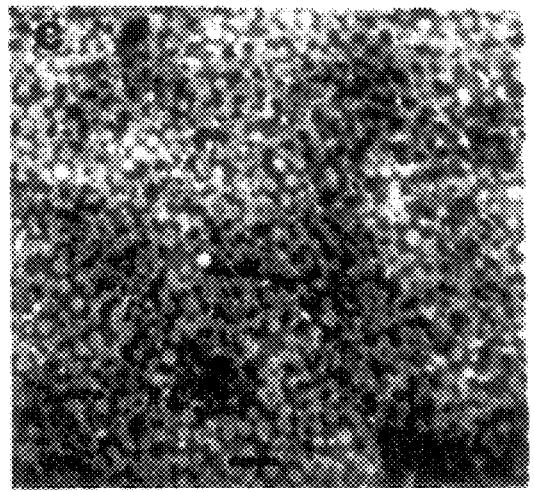
Figure 5B:
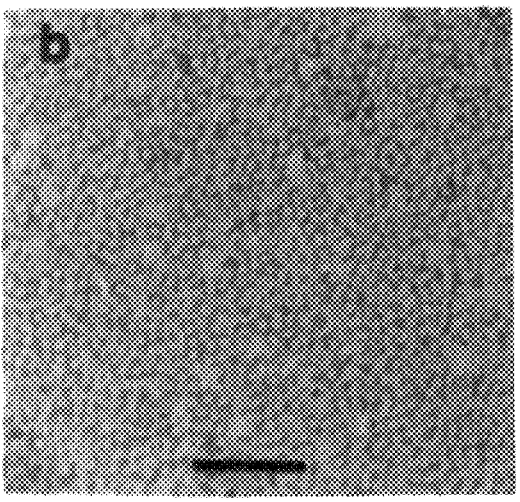
Figure 5D:
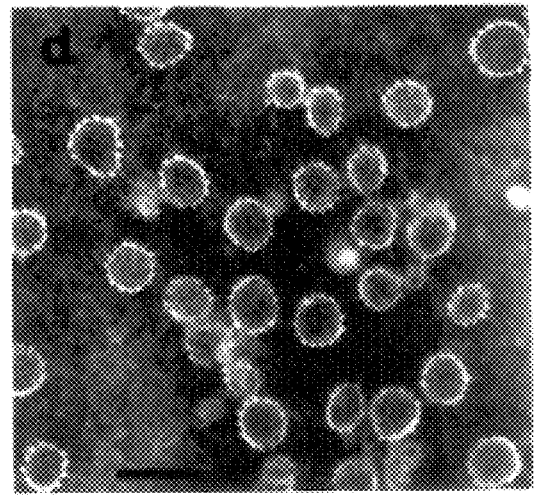

Relatively large quantities of HPV-11 L1 VLPs were prepared as starting material for the study of VLP disassembly and reassembly. HPV-11 L1 VLPs were isolated from recombinant baculovirus-infected High Five™ cells by CsCl and sucrose gradient centrifugation. The calculated purity of these L1 preparations, based on densitometric analysis of SDS/PAGE, ranged between 70–90% (see FIG. 1, lane 2). In addition, in linear sucrose gradients most of the protein migrated as expected for a mixture of individual and clumped VLPs (FIG. 4*a*), and in the electron microscope a mixture of intermediate and full-size (50–55 nm) articles were apparent (FIG. 5*a*).

The covalent and non-covalent interactions which stabilize the assembled L1 VLPs are not entirely known, but earlier work on papillomavirus VLPs and related polyomavirus virions and VLPs suggested the importance of ionic strength, divalent cations (Brady et al, *J. Virol.*, 23:717–724 (1977); Salunke et al, *Biophys. J.*, 56:887–900 (1987), and disulfide bonds (Sapp et al, *J. Gen. Virol.*, 76:2407–2512 (1995); Volpers et al, *Virology*, 200:504–512 (1994). In particular, Sapp and co-workers had demonstrated by immunoblotting that ~50 percent of the L1 protein of HPV-33 VLPs was disulfide-bonded into a range of larger oligomers with an apparent $M_r$ consistent with trimers of L1, and that mild reducing conditions partially broke down HPV-33 VLPs to the level of capsomeres (Sapp et al, *J. Gen. Virol.*, 76:2407–2412 (1995); Volpers et al, *Virol.*, 200:504–512 (1994). In our studies, in the absence of reducing agents only a portion of the HPV-11 L1 protein migrated on SDS/PAGE with an apparent $M_r$ of 55,000 Da (FIG. 1, Lane 1). Approximately 40% (the percentage varied between different VLP preparations) of the L1 protein of HPV-11 VLPs was disulfide-bonded into larger oligomers (FIG. 1, Lane 1), with predicted $M_r$ values of approximately 144,000 Da (possibly L1 trimer) and 210,000 Da (possibly L1 tetramer). The L1 oligomers did not migrate as a single band, and appeared to be heterogeneous in size. The ~200,000 Da oligomer was also observed on immunoblots by Sapp and coworkers (Sapp et al, *J. Gen. Virol.*, 76:2407–2412 (1995); Volpers et al, *Virol.*, 200:504–512 (1994), as part of a broad higher molecular weight band. These results indicate that a portion of the L1 proteins in HPV-11 VLPs are disulfide-linked into higher oligomers. To study the role of disulfide linkages and other interactions in VLP stability, a rapid screening assay for VLP disassembly was developed. Purified HPV-11 L1 VLPs, both before and after various treatments, were layered atop 30% sucrose cushions, centrifuged, and the distribution of L1 protein at the top and bottom of the 30% cushion was visualized by SDS/PAGE.

Intact VLPs were expected to pellet through the 30% sucrose cushion; non-aggregated capsomeres and L1 monomer were expected to remain on the top of the cushion. An example of this assay is shown in FIG. 2. To quantitate the relative disposition of L1 protein, the gels were digitized, the total intensity of the L1 bands at the top and the bottom of the cushion was determined, and then the percentage of the L1 staining intensity found at either position was calculated. The results of a number of such determinations are tabulated in Tables 1 and 2. As demonstrated in FIG. 2, the purified VLP starting material sedimented through the 30% sucrose, as predicted, with no L1 apparent at the top. However, upon incubation with a high concentration of the reducing agent β-mercaptoethanol (βME), L1 protein was found largely at the top of the 30% sucrose cushion, indicating that the reducing agent had disassembled the HPV-11 VLPs to smaller, non-aggregated components. Interestingly, maximal disassembly of the VLPs typically required exposure to a very high concentration of reducing agent (in this instance 5%, or 713 mM, βME) for a relatively long duration (~16 hours at 4° C.). Lower concentrations of reducing agent or shorter durations of reduction were not as reliably effective at VLP disassembly. Addition of a low concentration of a chelating agent did not enhance disassembly (FIG. 2 and Table 1)

In addition to reductants, the other important variables for quantitative disassembly of VLPs were found to be the ionic strength during the disassembly reaction and the solubility of the VLP starting material. As observed earlier for polyomavirus virions, lower ionic strength conditions destabilize VLPs (Brady et al, *J. Virol.*, 23:717–724 (1977), although Sapp et al, *J. Gen. Virol.*, 76:2407–2412 (1996) reported that generation of HPV-33 capsomeres from VLPs was insensitive to salt concentration between 0.15M and 0.6 M NaCl. For HPV-11 VLPs, maximum disassembly (~90%) of VLPs exposed to 5% βME for 16 hours was observed at "physiological" ionic strength (i.e., 0.15 M NaCl), but became correspondingly less effective as the ionic strength was increased (Table 1). The stabilizing effect of increased ionic strength could be partially overcome by incubating the VLPs with reducing agents for longer durations or at elevated temperatures. However, while incubating the VLPs with 5% βME for 120 hours at 4° C., or for 24 hours at 24° C. increased the extent of disassembly to 60–70% at 0.5 M NaCl, disassembly was still far from complete (data not shown). Furthermore, for quantitative disassembly, the degree of aggregation of the VLP starting material was also important. In the experiments reported here, the VLP solutions were dialyzed into different ionic strength buffers and stored at 4° C. until use in disassembly trials. After several days, particularly at 0.15 M NaCl, the solutions became slightly cloudy, indicating some degree of aggregation (although little or no precipitate was observed). Treatment of the clouded VLP solutions with reducing agents did not yield the same degree of disassembly as was observed with the initial soluble VLP solution, indicating that the aggregated VLPs were resistant to disassembly. However, upon removal of the aggregated material (which ranged from 10–50% of the total VLPs depending on the age of the preparation) by filtration, the remaining soluble VLPs again could be disassembled to the same extent as the initial soluble VLP starting material.

Interestingly, even at high concentrations of chelators, chelation of cations did not significantly influence VLP disassembly. Dialysis of VLPs into 200 mM EDTA or EGTA buffers (PBS-0.3 M NaCl, pH 7.4) led to no apparent disassembly, and the addition of 10 mM dithiothreitol (DTT) to the dialysis buffers had little effect (Table 2). The inability of high concentrations of chelators to disassemble VLPs was confirmed by electron microscopic analysis, although EDTA (but not EGTA) appeared to swell the VLPs slightly (data not shown). Either these concentrations of chelator are insufficient to extract tightly bound, structurally-important ions, or cations are not essential to maintaining VLP structural integrity. Conversely, addition of a concentrated aliquot of $NaHCO_3$ buffer (pH 9.6) to a solution of VLPs, to a final concentration of 200 mM carbonate (in PBS-0.3 M NaCl), caused significant breakdown of the VLPs (Table 2). Addition of DTT (to a final concentration of 10 mM), did not further enhance carbonate-induced breakdown. Incubation of VLPs with 200 mM carbonate/10 mM DTT is commonly used to denature HPV virions or VLPs in ELISAs (Favre et al, *J. Virol.*, 15:1239–1237 (1975); Christensen and Kreider, *J. Virol.*, 64:3151–3156 (1990); Christensen et al, *J. Gen. Virol.*, 75:2271–2276 (1994). The effect of carbonate appears to be buffer specific, and not merely a function of pH, as incubation of HPV-11 VLPs with pH 9.6 glycine buffer (200 mM final concentration) caused very little VLP breakdown, as measured by the 30% sucrose cushion assay (Table 2). Similarly, Brady et al, *J. Virol.*, 23:717–724 (1977), observed that carbonate buffer at alkaline pH, but not alkaline pH alone, dissociated polyomavirus virions. However, the specific effect of carbonate at pH 9.6 does not appear to be due to carbonate's potential chelating ability, as suggested by Brady et al, *J. Virol.*, 23:717–724 (1977), as 200 mM EDTA at pH 9.6 (+/−10 mM DTT) was completely ineffective at VLP disassembly (data not shown).

Example 2

Characterization of disassembled VLPs

Following long-term exposure to high concentrations of reducing agent, the purified VLPs appear to be broken down to the level of capsomeres. As shown in FIG. 3a, the disassembled VLPs generated by incubation with 5% βME for 16 hours at 4° C. migrated on 5–20% linear sucrose gradients with an average sedimentation coefficient of 11.3±1.5 S (n=5), determined relative to sedimentation standards. Larger species, with a calculated sedimentation coefficient of 16–18 S (perhaps dimeric capsomeres), and even pelleted materials were occasionally observed. However, less than 10% of the L1 was detected at the top of the gradient (expected position for L1 monomer) or in the pellet (expected position for intact VLPs or aggregated capsomeres), suggesting that the purified VLP starting material was largely disassembled to the level of individual capsomeres upon prolonged reduction. This conclusion is supported by electron microscopic analysis of VLPs following prolonged incubation with 5% βME, which depicted a field of homogeneous capsomeres (FIG. 5b) averaging 9.7±1.2 nm (n=15) in diameter, with occasionally a few larger aggregated structures apparent (monomeric L1 would not be detected with this technique). The estimated capsomere diameter is slightly smaller than that observed by cryo-electronmicroscopy (11–12 nm) (Baker et al, *Biophys. J.*, 1991; Hagensee et al, *J. Virol.*, 68:4503–4505, (1994); Belnap et al, *J. Mol. Biol.*, 259:249–263 (1996), perhaps due to shrinkage during electron microscope grid preparation. The data demonstrated in FIGS. 3a and 5b indicate that prolonged exposure to high concentrations of reductants quantitatively disassembles purified, soluble VLPs to a homogenous population of capsomeres.

Capsomeres generated from HPV-11 VLPs upon long term exposure to high concentrations of reducing agent contain structural epitopes found on intact VLPs. A panel of HPV-11-specific monoclonal antibodies has been described which react with intact HPV-11 L1 VLPs but not with "denatured" L1. These monoclonals include H11.F1, which has been demonstrated to recognize a dominant neutralizing epitope on HPV-11 virions, and H11.A3, a distinct non-neutralizing structure-dependent antibody (Christensen and Kreider, *J. Virol.*, 64:3151–3156 (1990); Christensen et al, *J.*

Figure 6A:
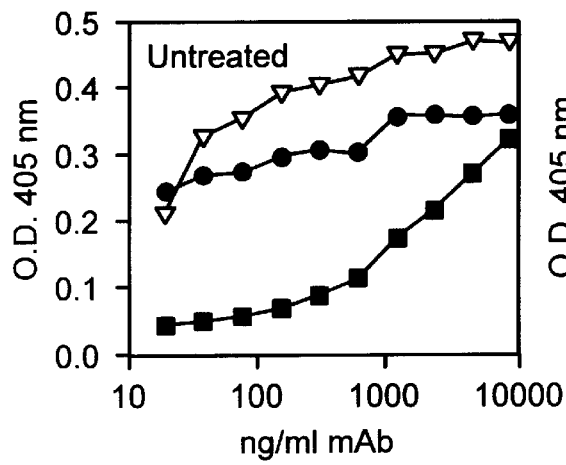
Figure 6B:
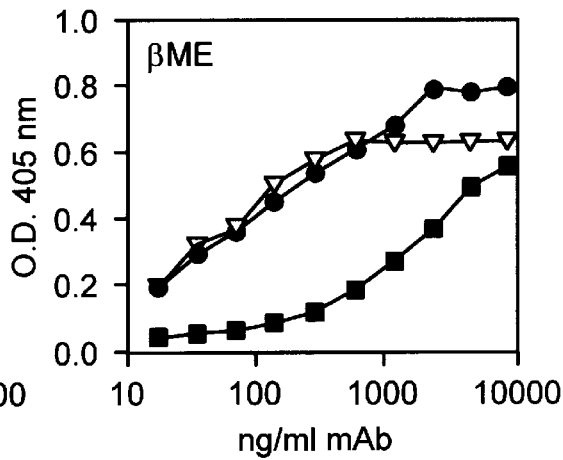
Figure 6C:
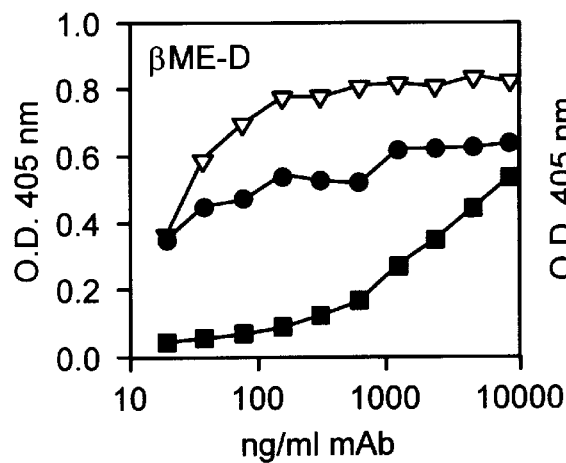
Figure 6D:
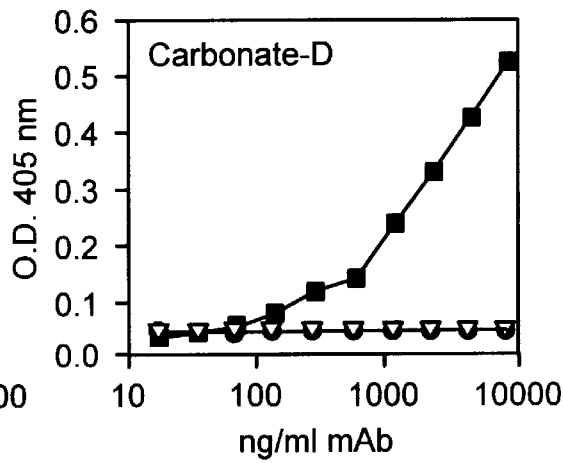

Virol., 64:5678–5681 (1990). As anticipated, H11.F1 and H11.A3 reacted strongly with the purified HPV-11 VLP starting material when analyzed by ELISA (FIG. 6a). However, these antibodies also reacted with capsomeres generated from the VLP starting material by exposure to reducing agent (FIG. 6b). Thus, capsomeres possess at least some of the structure-dependent epitopes found on the surface of intact VLPs and authentic virions, in agreement with studies performed by Li et al, J. Virol., 71:2988–2995 (1997) on HPV-11 capsomeres expressed in E. coli. These results further demonstrate that monoclonal antibodies H11.F1 and H11.A3, while requiring a "native-like" conformation for binding, are not VLP-dependent as has been previously described (Ludmerer et al, J. Virol., 71:3834–3839 (1997)).

In contrast, monoclonal antibodies H11.F1 and H11.A3 fail to recognize HPV 11 VLPs dissociated by treatment with carbonate buffer at pH 9.6 (data not shown; Christensen et al, J. Gen. Virol., 75:2271–2275 (1994). Carbonate treatment did not lead to a homogeneous solution of capsomeres, but instead appeared as an indistinct mixture of small objects, partially aggregated, when examined by electron microscopy (data not shown). This view was partially confirmed by analysis of carbonate-treated VLPs on 5–20% linear sucrose gradients, in which the L1 protein largely migrated at ~4 S, although a small population at 9–11 S was observed (FIG. 3b), in agreement with the effects of carbonate buffer (at pH 10.6, with 10 mM DTT) upon BPV virions (Favre et al, J. Virol., 15:1239–1247 (1975)). Finally, while treatment with glycine buffer at pH 9.6 did not dissociate VLPs to smaller, individual particles (Table 2), it did have some effect. VLPs treated with pH 9.6 glycine appeared in the electron microscope as a poorly-defined mixture of intact, and partially-broken down and aggregated VLPs (data not shown).

Example 3
Use of Isolated HPV-11 L1 Capsomeres to Produce Induce Virus-Neutralizing Antibodies Purified L1 capsomeres were used to produce polyclonal antisera in rabbits, and three-fold serial dilutions of these antisera along with antisera raised previously against recombinant HPV-11, 16 and 18 capsids, where tested against intact capsids of HPV types 11, 16 and 18. HPV-11 capsomere-specific and capsid-specific polyclonal antisera were each equally immunoreactive with intact HPV-11 capsids at all dilutions tested but did not react with HPV-16 or HPV-18 capsids. These results are consistent with previous observations made using HPV-11, 16 and 18 capsid-specific polyclonal antisera (Rose et al, J. Gen. Virol., 75:2445–2449 (1994)), indicating that HPV-11 isolated L1 capsomeres are highly immunogenic and retain genotype-restricted antigenicity exhibited by intact L1 capsids and native HPV virions. When tested in an in vitro neutralization assay involving infectious HPV-11 virions, post-immune HPV-11 L1 capsomere-specific polyclonal antisera exhibited a neutralization titer of $10^{-5}$–$10^{-6}$ which is comparable to that obtained with an antiserum raised against intact HPV-11 virions in vivo (Rose et al, J. Gen. Virol., (Id.)). Pre-immune sera from rabbits immunized with isolated L1 capsomeres exhibited no virus-neutralizing activity, nor did a polyclonal antiserum raised previously against HPV-16 capsids. Thus, isolated HPV-11 capsomeres display a highly immunogenic, genotype-restricted capsid neutralizing antigenic domain of HPV-11 virions and intact capsids, and should be a useful immunogen for the prevention of genital HPV disease.

TABLE 1

Disassembly of HPV-11 L1 VLPs'; Effects of reducing agents[a]

| Disassembly Condition | 0.15 M NaCl | | 0.3 M NaCl | | 0.5 M NaCl | |
|---|---|---|---|---|---|---|
| | Top | Bottom | Top | Bottom | Top | Bottom |
| Starting Material | 3.8 ± 0.7 | 96.3 ± 0.8 | 3.2 ± 1.4 | 96.8 ± 1.4 | 4.2 ± 0.3.4 | 95.9 ± 0.6 |
| 5% βME, 16 hr | 87.7 ± 3.2 | 12.4 ± 3.1 | 70.9 ± 12 | 29.1 ± 12 | 53.2 ÷ 6.8 | 46.8 ± 6.8 |
| 5 βME, 1 hr | 68.1 ± 11 | 31.9 ± 11 | 68.0 ± 10 | 32 ± 10 | — | — |
| 2% βME, 16 hr | 72.1 ± 2.7 | 27.9 ± 2.7 | 67.6 ± 21 | 32.3 ± 612 | — | — |
| 0.5% βME, 16 hr | 45.8 ± 18 | 54.2 ± 16 | 28.8 ± 16 | 71.2 ± 16 | — | — |
| 10 mM DTT, 16 hr | 44.5 ± 11 | 55.5 ± 11 | 43.8 ± 20 | 56.2 ± 20 | — | — |
| 10 mM DTT, 1 hr | 9.5 ± 6.4 | 90.5 ± 6.4 | — | — | — | — |
| 10 mM DTT, 5 mM EDTA, 16 hr | 55.9 ± 6.2 | 44.1 ± 6.2 | — | — | — | — |

[a]VLPs (0.5–1.0 mg/ml protein) were treated as indicated at 4° C., and the distribution of L1 across a 30% sucrose cushion was determined as described in the Methods section. Shown are the means of multiple determinations (n = 3–7) ± the standard deviation.

TABLE 2

Disassembly of HPV-11 L1 VLPs; Effects of chelators and buffers[a]

| Disassembly Condition | Top | Bottom |
|---|---|---|
| 200 mM EDTA, pH 7.4 | 4 ± 3 | 96 ± 3 |
| 200 mM EDTA, 10 mM DTT | 10 ± 6 | 90 ± 6 |
| 200 mM EGTA, pH 7.4 | 13 ± 11 | 87 ± 11 |
| 200 mM EGTA, 10, M DTT | 11 ± 6 | 89 ± 6 |
| 200 mM NaHCO$_3$, pH 9.6 | 81 ± 2 | 19 ± 2 |
| 200 mM NaHCO$_3$, 10 mM DTT | 74 ± 11 | 26 ± 11 |
| 200 mM glycine, pH 9.6 | 11 ± 1 | 89 ± 1 |
| 200 mM glycine, 10 mM DTT | 41 ± 12 | 59 ± 11 |

[a]VLPS (0.5–1.0 mg/ml protein) were treated as indicated for 16 hours at 4° C., and the distribution of L1 across of 30% sucrose cushion was determined as described in the Methods section. Shown are the averages of duplicate determinations ± the range.

The invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within that scope.

What is claimed is:

1. Stable human papillomavirus (HPV) capsomeres which (i) have a reduced capacity to assemble into virus-like particles (VLPs) relative to a corresponding non-modified HPV L1 protein, wherein reduced capacity means that said capsomeres assemble into VLPs less than 50% relative to a corresponding non-modified HPV L1 protein;

(ii) present at least one virus-neutralizing conformational epitope of the major capsid protein (L1) expressed by a native (wild-type infectious) HPV virus; and (iii) induce the production of HPV neutralizing antibodies.

2. The stable HPV capsomeres of claim 1, which are selected from the group consisting of HPV-6, HPV-11, HPV-16, HPV-18, HPV-30, HPV-31, HPV-33, HPV-35, HPV-39, HPV-42, HPV-43, HPV-44, HPV-45, HPV-51, HPV-52, HPV-54, HPV-55, HPV-56 and HPV-70 capsomers.

3. The stable capsomeres of claim 1, wherein said stable HPV capsomeres are HPV-11 capsomeres.

4. The stable capsomeres of claim 1, wherein said stable HPV capsomeres are produced by expression of a modified HPV L1 DNA which comprises a carboxyl-terminal deletion which inhibits or prevents VLP assembly.

5. The stable capsomeres of claim 4, wherein said carboxyl-terminal deletion results in the deletion of at least 30 amino acids of the carboxyl-terminal portion of the L1 protein.

6. The stable capsomeres of claim 5, wherein said modified HPV L1 DNA upon expression results in an L1 protein lacking from about 30 amino acids to about 86 amino acids of the carboxyl-terminal portion of the L1 protein.

7. The stable capsomeres of claim 4, wherein said HPV L1 DNA further comprises at least one addition, substitution or deletion modification which inhibits or prevents disulfide bond formulation.

8. The stable capsomeres of claim 7, wherein the modification comprises the deletion and/or substitution of at least one cysteine codon.

9. The stable capsomeres of claim 8, wherein at least one of said cysteine residue(s) is contained in the region of the L1 protein spanning residues 30 to 86, inclusive, relative to the carboxy terminal end of the L1 protein.

10. The stable capsomeres of claim 1, wherein said capsomeres are produced by the expression of an HPV L1 DNA which has been modified to introduce a mutation which inhibits capsomere-capsomere disulfide bond formation.

11. The stable capsomeres of claim 10, wherein said modification comprises the deletion and/or substitution of at least one cysteine codon.

12. The stable capsomeres of claim 1, wherein said HPV capsomeres induce the production of neutralizing antibodies in a human.

13. The stable capsomeres of claim 12, wherein said HPV are HPV-11 capsomeres.

14. A composition for eliciting neutralizing antibodies against a particular HPV type which comprises an amount of the stable HPV capsomeres of claim 1 sufficient to elicit neutralizing antibodies to said HPV upon challenge and a pharmaceutically acceptable carrier.

15. The composition of claim 14, wherein said composition consists essentially of said stable HPV capsomeres.

16. The composition of claim 14, wherein said stable HPV capsomeres are produced by expression of an HPV L1 DNA containing a modification which upon expression results in stable HPV capsomeres that are have a reduced capacity to assemble into virus-like particles, wherein reduced capacity means that said capsomeres assemble into VLPs less than 50% relative to a corresponding non-modified HPV L1 protein.

17. The composition of claim 16, wherein said modification results in the deletion of at least the 30 carboxyl-terminal amino acids of the HPV L1 protein and/or a deletion, addition or substitution modification which inhibits or prevents formation of a disulfide bond involved in VLP assembly.

18. The composition of claim 17, wherein said modification comprises the deletion and/or substitution of at least one cysteine residue.

19. The composition of claim 14, wherein the stable HPV capsomeres contained therein are selected from the group consisting of HPV-6, HPV-11, HPV-16 and HPV-18 capsomeres, or a mixture thereof.

20. The composition of claim 14, wherein said stable HPV capsomeres are produced by trypsin digestion of HPV virus-like particles or capsomeres, or by treatment with a compound that inhibits the oxidation of reactive sulfhydryls.

21. A method of conferring protection to HPV infection in a susceptible host comprising administering a prophylactically effective amount of stable human capsomeres according to claim 1.

22. The method of claim 21, wherein said stable HPV capsomeres are selected from the group consisting of HPV-6, HPV-11, HPV-16, HPV-18, HPV-30, HPV-31, HPV-33, HPV-35, HPV-39, HPV-42, HPV-43, HPV-44, HPV-45, HPV-51, HPV-52, HPV-54, HPV-55, HPV-56, HPV-70 capsomeres, and mixtures thereof.

23. The method of claim 22, wherein said stable HPV capsomeres comprise HPV-11 capsomeres.

24. The method of claim 21, wherein said stable capsomeres contain a carboxyl-terminal deletion which removes at least 30 amino acids of the carboxy-terminal portion of the L1 protein.

25. The method of claim 24, wherein said stable capsomeres lack from 30 to 86 amino acids of said HPV L1 protein.

26. The method of claim 21, wherein said stable HPV capsomeres are produced by expression of an HPV L1 DNA which has been modified to inhibit capsomere-capsomere disulfide bond formation.

27. The method of claim 26, wherein the modification comprises the deletion and/or substitution of at least one cysteine codon.

28. A diagnostic composition comprising a diagnostically effective amount of stable human papillomavirus capsomeres according to claim 1.

29. The diagnostic composition of claim 28, wherein said capsomeres are directly or indirectly attached to a detectable label.

30. An HPV L1 DNA that contains a modification that upon expression it results in the production of stable HPV capsomeres which have a reduced capacity to assembly into virus-like particles relative to a corresponding non-modified HPV L1 protein, wherein reduced capacity means that said capsomeres assembly into VLPs less than 50% relative to a corresponding non-modified HPV L1 protein, and which present at least one virus-neutralizing conformational epitope expressed by a native HPV virion.

31. The HPV L1 DNA of claim 30, which comprises a modification which inhibits or prevents the formation of at least one disulfide bond involved in VLP assembly.

32. The HPV L1 DNA of claim 31, wherein said modification comprises the substitution or deletion of at least one cysteine residue.

33. The HPV L1 DNA of claim 32, which further comprises a carboxyl terminal deletion which inhibits the formation of virus-like particles.

34. The HPV L1 DNA of claim 33, wherein said carboxyl-terminal deletion results in the elimination of at least 30 amino acids of the L1 protein.

35. The HPV L1 DNA of claim 34, wherein said carboxyl-terminal deletion results in the elimination of from about 30 to 86 amino acids of the L1 protein.

* * * * *